(12) United States Patent
Olszewski et al.

(10) Patent No.: US 9,036,778 B2
(45) Date of Patent: May 19, 2015

(54) SYSTEM AND METHOD FOR MEASURING THE THICKNESS OF A ZINC LAYER ON STEEL AND FOR MEASURING THE IRON CONCENTRATION IN A ZINC LAYER

(75) Inventors: Rigobert Olszewski, Bamberg (DE); Peter Helbig, Eckental (DE); Hanns-Werner Ortner, Erlangen (DE); Karl-Heinz Golz, Nürnberg (DE)

(73) Assignee: Rayonic Sensor System GmbH, Forchheim (DE)

( * ) Notice: Subject to any disclaimer, the term of this patent is extended or adjusted under 35 U.S.C. 154(b) by 392 days.

(21) Appl. No.: 13/533,154

(22) Filed: Jun. 26, 2012

(65) Prior Publication Data
US 2012/0328075 A1    Dec. 27, 2012

(30) Foreign Application Priority Data
Jun. 27, 2011  (DE) .......................... 10 2011 051 365

(51) Int. Cl.
| | | |
|---|---|---|
| *G01N 23/223* | (2006.01) | |
| *G01N 23/20* | (2006.01) | |
| *G01N 33/20* | (2006.01) | |
| *G01B 15/02* | (2006.01) | |
| *G01N 23/22* | (2006.01) | |

(52) U.S. Cl.
CPC ................ *G01N 33/20* (2013.01); *G01B 15/02* (2013.01); *G01N 23/20066* (2013.01); *G01N 23/2206* (2013.01); *G01N 23/223* (2013.01); *G01N 2223/61* (2013.01); *G01N 2223/076* (2013.01)

(58) Field of Classification Search
CPC .......... G01N 23/20066; G01N 23/205; G01N 23/2206; G01N 23/223; G01N 2223/076; G01N 2223/0763

USPC .................................... 378/46, 50, 88, 89, 90
See application file for complete search history.

(56) References Cited

U.S. PATENT DOCUMENTS

| | | | | |
|---|---|---|---|---|
| 3,287,560 A | * | 11/1966 | Morgan ...................... | 250/385.1 |
| 3,497,691 A | * | 2/1970 | Chen ................................ | 378/50 |
| 3,754,138 A | * | 8/1973 | Kurstedt et al. .................. | 378/50 |
| 3,843,884 A | | 10/1974 | Evans | |
| 5,187,727 A | * | 2/1993 | Vogler et al. ..................... | 378/50 |

(Continued)

FOREIGN PATENT DOCUMENTS

| | | |
|---|---|---|
| DE | 199 19 990 B4 | 11/2000 |
| DE | 103 45 754 A1 | 4/2005 |

(Continued)

*Primary Examiner* — Glen Kao
(74) *Attorney, Agent, or Firm* — Bryan W. Bockhop; Bockhop & Associates, LLC

(57) ABSTRACT

A Compton radiation detection device for determining of Compton radiation of iron, includes a sensor and a filter arrangement. The filter arrangement is adapted such that the radiation emitted by a test object due to Compton scattering passes a nickel layer and an iron layer before being detected by the sensor. A dispersive ionization chamber includes an ionization chamber having a plurality off ionization volumes and a window. Each ionization volume includes an electrode. Radiation can enter through the window. The ionization volumes are arranged in a beam propagation direction behind each other. Radiation having lower energy is statistically absorbed in ionization volumes located more proximal to the window. Radiation having higher energy is statistically absorbed in the ionization volumes located more distal from the window.

23 Claims, 6 Drawing Sheets

(56) References Cited

U.S. PATENT DOCUMENTS 5,579,362 A 11/1996 Matsuura et al.
7,356,114 B2 4/2008 Kataoka et al.

FOREIGN PATENT DOCUMENTS

| EP | 0 465 797 A2 | 1/1992 |
|----|---|---|
| WO | 2009/129479 A1 | 10/2009 |

* cited by examiner

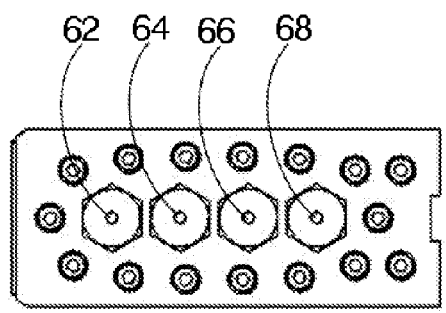
FIG. 5
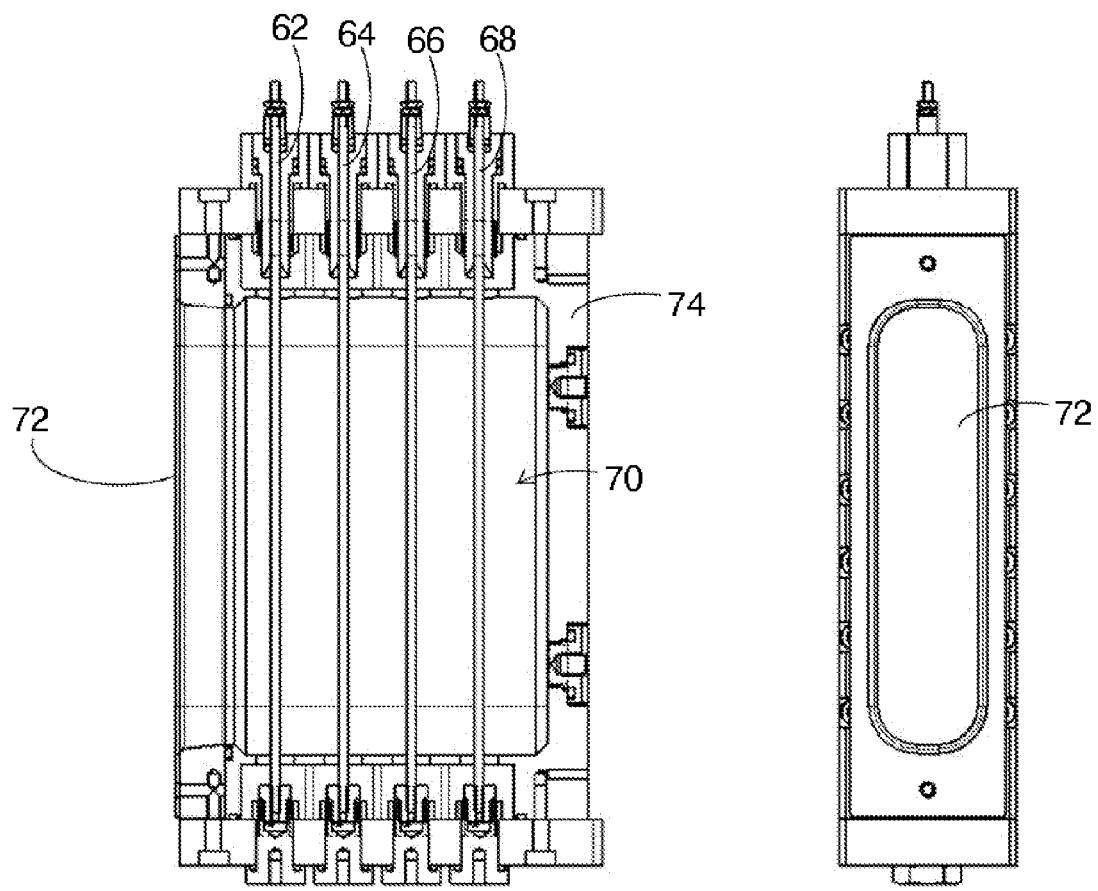
FIG. 6
FIG. 7

SYSTEM AND METHOD FOR MEASURING THE THICKNESS OF A ZINC LAYER ON STEEL AND FOR MEASURING THE IRON CONCENTRATION IN A ZINC LAYER

CROSS-REFERENCE TO RELATED APPLICATION(S)

This application claims the benefit of German Patent Application No. 10 2011 051 365, filed Jun. 27, 2011, the entirety of which is hereby incorporated herein by reference.

BACKGROUND OF THE INVENTION

1. Field of the Invention

The invention relates to a system and method for measuring the thickness of a zinc layer on steel and/or for measuring the iron content and iron concentration, respectively on a zinc layer. Further thereto to the invention relates to the use of a dispersive ionization chamber for material testing.

2. Description of the Related Art

Steel sheets are galvanized in order to make them more corrosion-resistant. The determination of the thickness of the zinc layer is essential in order to ensure on the one hand a predetermined minimum thickness of the zinc layer for guaranteeing the corrosion—resistance and on the other hand for the purposes of economizing resources that no too thick zinc layers are applied.

EP 0 465 797 B1 discloses an apparatus for measuring the iron content in zinc layers and/or for measuring the thickness of a zinc layer by x-ray fluorescence. The apparatus disclosed therein has the disadvantage that a zinc application of maximum of 350 g/m$^2$ can be determined. A higher zinc application cannot be measured by such apparatus.

Particularly for manufacturing crash barriers and for manufacturing trucks it is desired to apply a zinc application of more than 350 g/m$^2$ on a steel sheet. Further, it is desired that in strip zinc coating lines a verification system is implemented which can determine a zinc application over a larger measurement range.

During steel manufacturing a strip like steel is coated with zinc for increasing resistance against corrosion. Thereafter, a so called galvannealing process may be performed. Thereby, galvanized steel is subsequently heated to approximately 500° C. to approximately 600° C. By such galvannealing iron diffuses into the zinc layer such that inter metal compositions and an inter metal alloy between zinc and iron is generated. This inter metal composition is of major importance for further processing of the coated steel and for the adherence properties of the zinc layer. Hereby, it is essential that during the manufacturing method the iron ratio in the zinc layer is adjusted within the narrow bounds in order that the method is performed reproducible. Accordingly, it is important, that the iron content in a zinc layer is verified in a non-destructive manner.

SUMMARY OF THE INVENTION

The disadvantages of the prior art are overcome by the present invention which, in one aspect, is a method and system that may measure the thickness of a zinc layer on steel in a broad range.

In another aspect, the invention is a method and apparatus for measuring the iron content of a zinc layer.

In at least one representative embodiment, the invention includes a determination apparatus that is adapted to determine the thickness of a zinc layer on an iron layer of a test object and the iron content in a zinc layer on an iron layer of the test object. The determination apparatus comprises an x-ray source emitting x-ray radiation on the test object having the zinc layer on the iron layer. The determination apparatus comprises a first fluorescence determination device for determining a first fluorescence radiation based on iron in the test object scattered under a first angle segment from the test object. The determination apparatus comprises a Compton determination device determining a Compton scattering based on iron in the test object scattered under a first angle segment from the test object. The determination apparatus comprises a second fluorescence determination device determining a second fluorescence radiation based on iron from the test object scattered under a second angle segment from the test object, and a third fluorescence determination device determining a third fluorescence radiation based on the zinc in the test object scattered under a second angle segment from the test object. A first analyzing device is adapted to determine the thickness of the zinc layer on the iron layer of the test object based on the first fluorescence radiation and the Compton radiation. A second analyzing device is adapted to determine the iron content in the zinc layer based on the first fluorescence radiation, the second fluorescence radiation and the third fluorescence radiation.

An embodiment of the invention may also include a zinc layer thickness determination apparatus adapted to determine the thickness of a zinc layer on an iron run layer of a test object. The zinc layer thickness determination apparatus comprises an x-ray source emitting x-ray radiation to the test object having the zinc layer on the iron layer. The zinc layer thickness determination apparatus comprises a first fluorescence determination device determining a first fluorescence radiation based on iron in the test object scattered under a first angle segment from the test object, and a first Compton determination device determining a Compton scattering based on iron in the test object scattered under a first angle segment from the test object. A first analyzing device is adapted to determine the thickness of the zinc layer on the iron layer of the test object based on the first fluorescence radiation and the Compton radiation.

An embodiment of the invention may also include an iron content determination apparatus adapted to determine the iron content (iron fraction) in a zinc layer on an iron layer of a test object. The iron content determination apparatus comprises a first x-ray source emitting x-ray radiation on the test object having the zinc layer on the iron layer. The iron content determination apparatus further comprises a first fluorescence determination device determining a first fluorescence radiation based on iron in the test object scattered under a first angle segment from the test object, a second fluorescence determination device determining a second fluorescence radiation based on iron in the test object scattered under a second angle segment from the test object, and a third fluorescence determination device determining a third fluorescence radiation based on iron in the test object scattered under a second angle segment from the test object. A first analyzing device is adapted to determine the iron content in the zinc layer based on the first fluorescence radiation, the second fluorescence radiation and the third fluorescence radiation.

The expression angle is to be interpreted such that it comprises an angle having a tolerance band, i.e. it forms an angle range.

The test object may be strip like steel, for example. Preferably the x-ray radiation is emitted perpendicular on the surface of the test object. The first fluorescence detection device, the second fluorescence detection device, the third fluorescence detection device and/or the Compton detection device may comprise an ionization chamber. The ionization chamber may comprise xenon or preferably krypton.

A plurality off first fluorescence detection devices, second fluorescence detection devices, third fluorescence detection devices and/or Compton detection devices may be arranged symmetrically to the x-ray beam. Thereby, corrugation of the test object or adjustment errors may be compensated.

The determination of the iron content in the zinc layer is important in order to determine consequently the thickness of the zinc layer more accurately.

The center of the first angle segment and the first angle segment, respectively can range from approximately 45° to approximately 90° with respect to the surface of the test object. Preferably the center of the first angle segment and the first angle segment, respectively may arrange from approximately 60° to approximately 85°, most preferred may range from approximately 70° to approximately 80° with respect to the surface of the test object. In this angle range both the Compton scattering as well as the fluorescence radiation of iron at atoms may be determined.

The x-ray radiation emitted on the test object is in an energy range of less than 50 keV. In order to generate the Compton scattering the primary x-ray radiation ranges in an energy range from approximately 35 keV to approximately 45 keV, most preferably in a range from approximately 39 keV to approximately 41 keV. The zinc-k-alpha-line based on the fluorescence is located at approximately 8.6 keV. The Compton scattering ranges in an energy range from approximately 25 to approximately 40 keV. In the first angle segment both the Compton scattering and the first fluorescence scattering based on iron in the test object is determined. Thereby, the thickness of the zinc layer above the iron layer may be determined. In case of a thin zinc layer, such as thinner than 250 g/m$^2$, the signal based on the first fluorescence radiation is more suitable for determining the thickness of the zinc layer. In case the zinc layer is comparably thick, such as thicker than 250 g/m$^2$, the signal based on the Compton scattering is more suitable for determining the thickness of the zinc layer.

The center of the second angle segment and the second angle segment, respectively may range from approximately 0° to approximately 45°, preferably range from approximately 10° to approximately 40°, most preferably may be in the range having an angle smaller than 35° with respect to the surface of the test object. The center of the second angle segment, and the second angle segment, respectively may be located at approximately 30°, preferably may be located in a range smaller than 30° with respect to the surface of the test object.

The Compton radiation detection device may be adapted such that the Compton scattering passes a zinc layer and an iron layer before it is detected by a sensor. The sensor may be an ionization chamber filled with the xenon preferably krypton. The ionization chamber may be configured for absorbing photons having energy in a range from approximately 25 keV to approximately 40 keV. The nickel layer may have a thickness from approximately 13 μm+/−3 μm, and the iron layer may have a thickness of approximately 25 μm+/−5 μm. The combination having a nickel filter and an iron filter is particularly suitable, since a portion of the radiation absorbed by nickel is transformed into fluorescence radiation of nickel. The fluorescence radiation of nickel is absorbed by iron particularly strong. The suppression of the zinc fluorescence radiation of such combination is particularly efficient without affecting the transmission of the Compton scattering.

By such filter arrangement the interfering zinc fluorescence radiation is suppressed particularly efficient. By such filter arrangement the less interfering iron fluorescence radiation is also suppressed, however to a small extent. Such filtering causes that merely radiation based on Compton scattering is entering the Compton detection device. Such radiation has energy of more than approximately 25 keV. The applicant reserves the right to direct claims to the filter arrangement having a nickel filter and an iron filter.

At the first fluorescence detection device an iron layer may be arranged which is passed by the iron fluorescence radiation. The iron layer may be an iron sheet having a thickness of approximately 25 μm+/−5 μm. Interfering and undesired zinc fluorescence radiation is suppressed by the iron layer.

At least one of the fluorescence detection devices and/or the Compton detection device may be a dispersive ionization chamber. At least one of the fluorescence detection devices and/or the Compton detection device may be formed by a dispersive ionization chamber. The dispersive ionization chamber comprises at least two ionization volumes each comprising one or a plurality of reading electrodes. The ionization volumes are arranged such consecutively that the ionization volume located in direction of the beam in the front position forms an absorption media for an ionization volume arranged in the beam propagation direction behind it. The ionization volumes may be read separately from each other. Each ionization chamber comprises a single collection electrode. The radiation must pass the ionization volumes consecutively. Thereby, readily absorbable components and spectra, respectively of the radiation are preferably converted in the front ionization volumes of the dispersive ionization chamber by ionization into an electric signal. Hard radiation and a spectrum having higher energy, respectively is converted in the rear ionization volume in a significant extent. Thereby, the spectrum composition of radiation may be determined by the radiation converted in the different ionization volumes in an electric signal. The ionization volumes may be located in a chamber filled with a suitable gas, such as an inert gas, preferably krypton and/or argon. The applicant reserves the right to direct claims to this aspect of the invention.

The dispersive ionization chamber comprises an ionization chamber having a plurality of ionization volumes, wherein one electrode is assigned to each ionization chamber, and one window, through which radiation may enter, wherein the ionization volumes are arranged in the beam propagation direction behind each other such that radiation having higher energy is statistically absorbed in the ionization volumes located more proximal to the window and radiation having higher energy is absorbed statistically in ionization volumes located more distal from the window. Each ionization volume in the ionization chamber may have one electrode.

The electrodes may be arranged in the beam propagation direction behind each other. X-ray radiation entering through the window into the dispersive ionization chamber passes first the ionization volume assigned to the first electrode, and successively further ionization volumes, respectively assigned to a second electrode, a third electrode and a fourth electrode.

At least one electrode may extend perpendicular to the beam propagation direction. The ionization volumes may be located in an ionization zone or ionization chamber filled with the inert gas.

A current measuring device may be connected to each of the electrodes and the dispersive ionization chamber may be adapted such that absorption of the x-ray quantum generates charge collected by one of the electrodes and detected by the respective current measuring device.

The invention relates also to use of a dispersive ionization chamber for material testing. The invention discloses a material test device having the above mentioned dispersive ionization chamber.

The Compton detection device and the first fluorescence detection device may be formed integral, such as by the dispersive ionization chamber. The second fluorescence detection device and the third fluorescence detection device may be formed integral by a dispersive ionization chamber. The expression integral is to be interpreted such that it means realized by one component and/or by a single piece.

An embodiment of the invention may also include a thickness measuring device having the above mentioned dispersive ionization chamber. Thus, the invention relates also to the use of a dispersive ionization chamber for determining the thickness of a material, particularly of a strip like material, such as a steel strip material. An x-ray source can direct x-ray radiation on a test object, for example perpendicular to the surface thereof, wherein the x-ray radiation passes the test object. At the side that is opposite to the x-ray source, of the test object a dispersive ionization chamber may be arranged. The dispersive ionization chamber detects the x-ray radiation that passed the test object. By means of the received x-ray spectrum the material composition of the test object may be determined. By means of the intensity of the x-ray beam after passing the test object as determined by the dispersive ionization chamber and by means of the material composition the thickness of the strip material may be determined. Based on the material composition the attenuation coefficient may be determined which may be stored for a certain number of materials in the system, for example in a table. This system and method is well-suited for strip material comprising alloy and/or a plurality of layers stacked above each other. By means of the spectrum determined by the ionization chamber it is possible to determine which elements and compounds, respectively the x-ray beam must pass before entering in the dispersive ionization chamber. The applicant reserves the right to direct claims to this aspect of the invention.

Ionization chambers are used for intensity measurements of x-ray radiation and gamma radiation. This allows thickness measurements (and/or measuring the coating weight per unit area) of a uniform test object. If the test object is comprised by different components in an unknown composition, the thickness measurement is obviated by the different absorption of said components. If the dependency of the absorption of the different components of the radiation energy differs from each other, the thickness measurement can be performed by an attenuation measurement for the different energies.

One application is found in the field of aluminum alloys. There are aluminum alloys having additions of heavy metals such as zinc or copper or metals having an even higher atomic number. In such case the dispersive ionization chamber is well suited for determining the exact composition and to allow a measurement of the thickness. This is particularly well suited for the production of aluminum films.

A further application is measuring of a non-uniform test object comprising materials having a different absorption, such as during the manufacturing of flat conductors and cables, which comprise wires made of copper betted in a plastic matrix, for example. It has to be distinguished between the coating grade of the wires and the thickness of the plastic coating. A measurement using different energies can separate these quantities. A further application is measuring of metal layers on a plastic carrier. Also in this case the energy reduction by absorption differs between the metal layer and the plastic carrier such that by a measurement using two energies the thickness of the two components may be determined.

Most appropriate the measurements using the different radiation energies are performed at the same location of the test object. Therefore, the dispersive ionization chamber may be used. The measurement is performed by a radiation source emitting different radiation energies. This is possible with most of the x-ray sources available. A comparison between the signals from the different ionization volumes of the dispersive ionization chamber results in an indicator for the energetic composition of the radiation entering the dispersive ionization chamber. A further comparison with the energetic composition of the radiation without test object allows determining the energetic absorption of the test object.

The first analyzing device may be adapted to calculate a weighted average based on the fluorescence radiation and the Compton scattering for determining the thickness of the zinc layer. The first analyzing device may be adapted to determine the thickness of the zinc layer merely from the first fluorescence radiation, if the thickness of the zinc layer is below a first threshold. The first analyzing device may determine the thickness of the zinc layer merely based on the Compton scattering, if the thickness of the zinc layer is above a second threshold. The first analyzing device may calculate the thickness of the zinc layer based on the first fluorescence radiation and the Compton scattering, if the thickness of the zinc layer is between the first and second threshold. Since the first analyzing device uses both the first fluorescence radiation and the Compton scattering for determining the thickness of the zinc layer, accuracy and consistency of the measurement results may be increased. Further, it is possible to evaluate a broad measurement range.

The first analyzing device may be adapted to determine the thickness of a zinc layer recursively based on the first fluorescence radiation and the Compton scattering. The first analyzing device may be adapted to determine the thickness of a zinc layer exclusively from the first fluorescence radiation, if the thickness of the zinc layer is lower than a first threshold. The first analyzing device may determine the thickness of the zinc layer based on the Compton scattering, if the thickness of the zinc layer is higher than a second threshold value. A first analyzing device may be adapted to determine the thickness of a zinc layer recursively from the first fluorescence radiation and the Compton radiation, if the thickness of the zinc layer is between the first and second threshold value. Based on this evaluation of the measurement results may be improved on the one hand and on the other hand the measurement range can be increased.

The first analyzing device may be adapted to observe during determining the thickness of the zinc layer the iron content in the zinc layer. Thereby the determination of the thickness of the zinc layer may be further improved.

An embodiment of the invention may also include a method for determining the thickness of the zinc layer on an iron layer of a test object and for determining the iron content in a zinc layer on an iron layer of the test object. X-ray radiation is emitted on the test object with the zinc layer on the iron layer, for example under an angle of approximately 90° with respect to the surface of the test object. A first fluorescence radiation based on iron in the test object is determined, which is scattered in a first angle segment from the test object. Further, a second fluorescence radiation due to iron is determined, which is scattered in a second angle segment from the test object. A third fluorescence radiation due to zinc in the test object is determined, which is scattered in a second angle segment from the test object. A Compton scattering due to iron in the test object is determined which is scattered in a first angle segment from the test object. The iron content in the zinc layer is determined from the first fluorescence radiation, the second fluorescence radiation and the third fluorescence radiation. The thickness of the zinc layer on the iron layer of the test object is determined from the first fluorescence radiation and the Compton scattering.

The method may be further configured as has been described before with respect the apparatus. Further, apparatus may be further configured as is described in the following with respect to the method.

An embodiment of the invention may also include a method for determining the thickness of a zinc layer on the iron layer of a test object. X-ray radiation is emitted on the test object with the zinc layer on the iron layer, preferably approximately perpendicular to the surface of the test object. A first fluorescence radiation due to iron in the test object is determined, which is scattered in a first angle segment from the test object. Further, Compton scattering due to iron in the test object is determined, which is scattered in a first angle segment from the test object. The thickness of the zinc layer on the iron run layer of the test object is determined from a first fluorescence radiation and the Compton scattering.

Further, an embodiment of the invention may also include a method for determining the iron content in a zinc layer on an iron layer of a test object. X-ray radiation is emitted on the test object having the zinc layer on the iron layer, preferably approximately perpendicular to the surface of the test object. The fluorescence radiation due to iron in the test object is determined, which is scattered in a first angle segment from the test object. A second fluorescence radiation due to iron in the test object is determined, which is scattered in a second angle segment from the test object. Further, a third fluorescence radiation due to zinc in the test object is determined, which is scattered in a second angle segment from the test object. The iron content in the zinc layer is determined from the first fluorescence radiation, the second fluorescence radiation and the third fluorescence radiation.

The step of detecting the thickness of the zinc layer can comprise the step of determining the weighted average from the first fluorescence radiation and the Compton radiation. The step of determining the thickness of the iron layer can comprise the step of iteratively processing the first fluorescence radiation and the Compton scattering. The step of determining the thickness of the iron layer may comprise the step of taking into account the iron content of the zinc layer.

An embodiment of the invention may also include the use of a dispersive ionization chamber for material testing by x-ray radiation. The x-ray radiation may pass the test object, scattered by the same and/or reflected by the same, whereby secondary x-ray radiation is generated. The secondary x-ray radiation may be used for determining the materials composition and/or the thickness of the test object.

These aspects are achieved by a Compton detection device and a dispersive ionization chamber. These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

FIG. 5-7 show views of a dispersive ionization chamber from different perspectives.

DETAILED DESCRIPTION OF THE INVENTION

Figure 1:
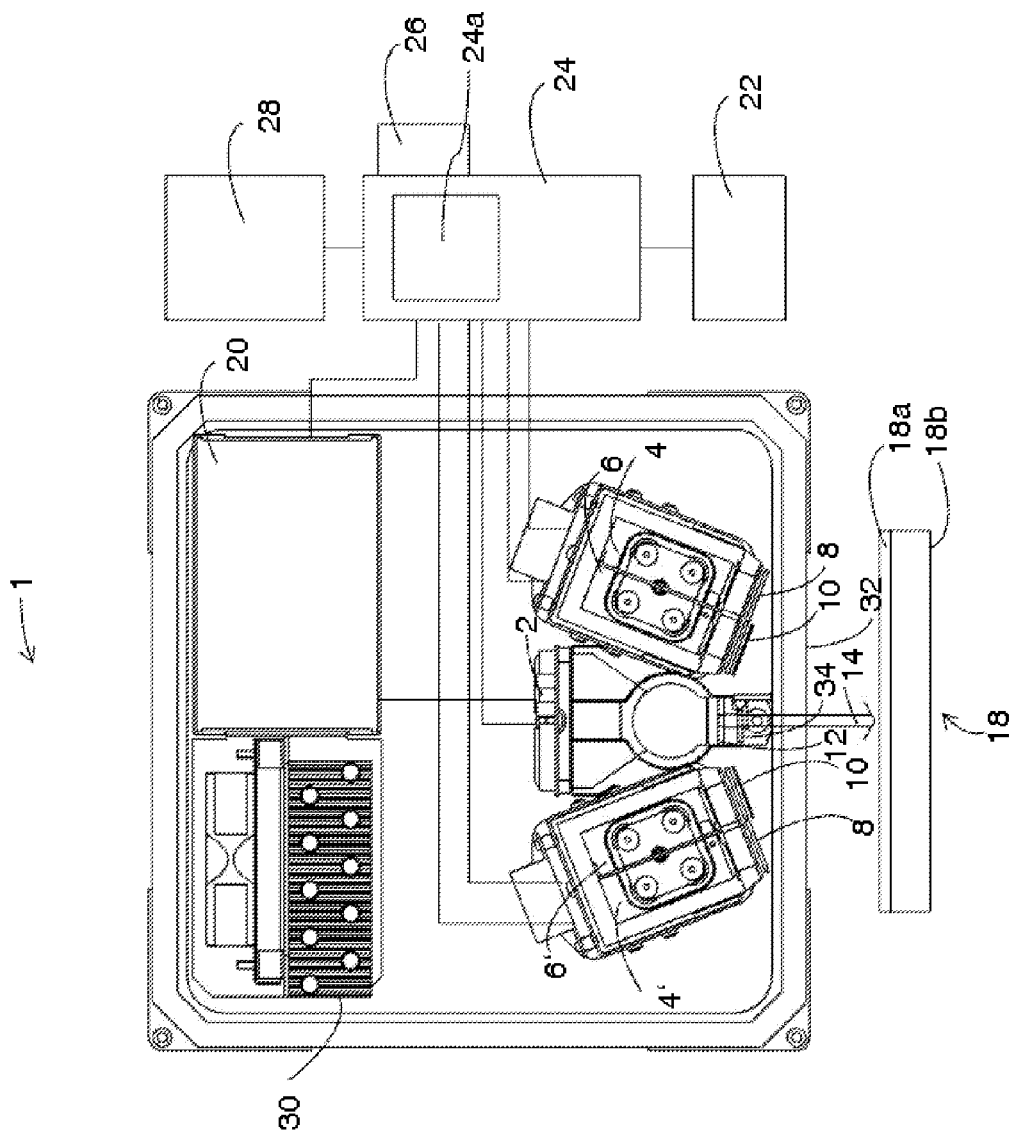
FIG. 1 is a schematic view of a zinc layer thickness determination apparatus.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

Reference is made to FIG. 1 showing a zinc layer thickness determining apparatus 1. The zinc layer thickness determination apparatus 1 is adapted to measure the thickness of a zinc layer 18a on an iron layer 18b of the test object 18, for example strip like steel. An x-ray source 2 emits an x-ray beam 14 passing a pre-filter 12 comprising zinc. The pre-filter 2 has a thickness of about 1 μm to about 10 μm. The x-ray beam 14 impinges approximately perpendicular on the zinc layer 18a and on the iron layer 18b of the test object 18. The test object 18 is shown in the schematic view of FIG. 1 magnified with respect to the zinc layer thickness determination apparatus 1.

The x-ray source 2 is supplied with a high-voltage from a high-voltage device 20. A heat exchanger dissipated the lost heat generated in the high-voltage device 20 into the environment. The x-ray source 2 comprises a diaphragm adjusting the cross-section of the x-ray beam to the desired dimension of approximately 25 mm×approximately 80 millimeter. The primary x-ray beam 14 pass a measurement window 32 before impinging on the test object 18.

A first ionization chamber 4 is formed as first fluorescence detection device. A second ionization chamber 4' is also formed as first fluorescence detection device. A third ionization chamber 6 and a fourth ionization chamber 6' form a Compton detection device. The ionization chambers are preferably filled with the inert gas krypton ensuring a comparably high sensitivity for radiation having energy of more than 25 keV. The first ionization chamber 4 and the second ionization chamber 4' are arranged symmetrically to the x-ray beam 14. The third ionization chamber 6 and the forth ionization chamber 6' are arranged symmetrically to the x-ray beam 14. Thereby, it may be ensured that adjustment errors and corrugation of the test object 18 can be eliminated.

The test object 18 scatters the fluorescence radiation and the Compton radiation through the measurement window 32 to the ionization chambers 4, 4', 6 and 6' as secondary x-ray radiation. In front of the measurement windows of the ionization chambers 4, 4', 6 and 6' an iron film having a thickness of approximately 25 μm+/−5 μm is located. This iron film ensures that the K-Alpha-line of zinc at approximately 8.6 keV is attenuated. This fluorescence radiation of zinc is undesired during measuring the thickness of the zinc layer. The K-Alpha-line of iron at approximately 6.4 keV can pass the iron filter 8.

In front of the measurement window of the Compton detection device 6 a nickel film having a thickness of approximately 13 μm+/−4 μm is located. The nickel film converts the fluorescence radiation of iron in fluorescence radiation of nickel. The fluorescence radiation of nickel is suppressed by the iron filter 8 efficiency located in the propagation direction behind the nickel filter. Accordingly, the third and fourth ionization chamber 6, 6' primarily analyze Compton scattering from iron.

The x-ray source 2 and the ionization chambers 4, 4', 6, 6' are connected to the first analyzing device 24a in a controller 24. An input device 22 and an output device 28 are also connected to the controller 24. Further, the controller 24 comprises an interface 26 for connecting to a process control system. The first analyzing device 24a may issue to the high-voltage device 20 a high-voltage value indicating the voltage required for supplying the x-ray source 2.

In the following the operation of the first embodiment of the invention is explained. The invention takes a back scattering of x-ray radiation in an energy range of less than 50 keV into account. It is known that a back scattering in the x-ray range that is composed from different compositions takes place, if an object is irradiated with x-ray radiation.

For a test object comprising galvanized steel the types of back scattering discussed in the following result. The x-ray fluorescence is based on an excitation of atoms by primary x-ray radiation 14. The excited atoms return to their ground state and emit a characteristic x-ray radiation ranging in an energy range of several keV. The K-Alpha-line of iron 18b is located at approximately 6.4 keV and the K-Alpha-line of zinc is located at approximately 8.6 keV. In the test object 18 discussed for of this embodiment the intensity of the iron line decreases due to the shading due to an increasing layer of zinc 18a. The intensity due to the zinc line increases. The material depth from which fluorescence radiation can reach the ionization chamber corresponds to approximately the absorption length of the emitted radiation in the irradiated material. The monitoring depth, i.e. the measurement range, corresponds to a multitude of the absorption length from approximately 0 to approximately 40 μm. Therefrom, results a practical measurement range from approximately 0 to approximately 350 $g/m^2$, if x-ray fluorescence radiation is used, for determining the thickness of the zinc layer 18a.

A second possibility for determining the thickness of the zinc layer 18a on iron 18b is analyzing the Compton back scattering. The Compton scattering is scattering of x-ray radiation on weak bound electrons in the irradiated material. The Compton scattering is back scattered with energy corresponding energy of the incident zinc x-ray quantum reduced by the impact energy of the electron. In a technical application the energy of the back scattered Compton radiation is more than 20 keV, particularly approximately 25 keV to approximately 40 keV. The intensity of the Compton back scattering depends from the type of material, since x-ray radiation is absorbed in different materials in a different manner. Zinc and iron absorb x-ray radiation approximately to the same extent. The Compton scattering of zinc and iron is different, since the zinc layer 18a comprises less electrons and therefore scattering centers. The intensity of the Compton scattering is reduced slightly by an increasing the thickness of the zinc layer.

The absorption length of the Compton scattering in an irradiated material is higher than 100 μm depending on the energy of the primary photons. Accordingly, the observation depth is in the magnitude of 100 μm and more. Therefrom, results a measurement range of up to approximately 800 $g/m^2$, which can be increased by higher energy of the x-ray radiation, for example up to 2000 $g/m^2$.

Besides the Compton effect, which is based on the inelastic scattering of bounded electrons, there is also inelastic scattering at the atoms, i.e. Rayleigh scattering. The scattering at the atomic cluster and at the single atoms, respectively has similar energy properties as Compton scattering. Since the energy relationships and the results of these processes are analog to the Compton effect these processes are regarded in the context of the present invention as the Compton effect.

Figure 2:
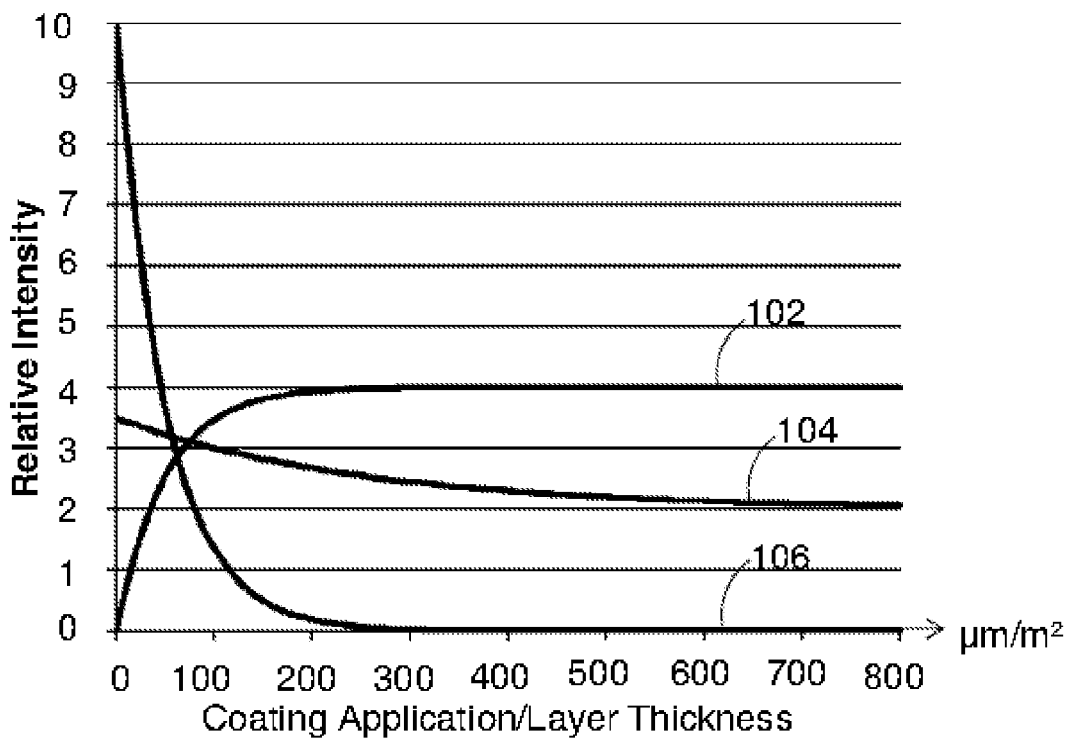
FIG. 2 shows the relative intensities of the back scattering of the fluorescence radiation as well as the Compton scattering as a function of the thickness of the zinc layer.

FIG. 2 shows the relative intensities of the back scattering at the test object 18 for fluorescence radiation and Compton scattering depending on the thickness of the zinc layer. The line 102 shows the fluorescence of zinc, the line 104 shows Compton scattering at electrons of the iron atoms and the line 106 shows the fluorescence due to iron. The fluorescence radiation of zinc 102 is suppressed by detecting the zinc layer, since it resides on a similar energy level as the fluorescence radiation of iron and comprises a slope opposite thereto.

According to the invention for determining the thickness of the zinc layer 18a both the x-ray fluorescence and the back scattering at higher x-ray energies, such as Compton scattering, are used. For determining the thickness of the zinc layer 18a different physical effects are combined, such as x-ray fluorescence and higher energy radiation, such as Compton scattering.

Since fluorescence radiation and the Compton radiation comprise different monitoring depth, as has been discussed before, by the combination of the different effects a zinc thickness determination apparatus 1 can be developed determining the thickness of the zinc layer 18a over a broad range with a high accuracy. The thickness of the zinc layer can be determined in a range of approximately 0 to approximately 800 $g/m^2$ and also up to approximately 1000 $g/m^2$. With this measurement range the thickness of a zinc layer in all currently used strip materials having hot galvanizing may be measured. The invention generates with merely a single primary beam 14 a plurality of secondary beans, i.e. iron fluorescence radiation and secondary radiation due to the Compton effect.

The first ionization chamber 4 and the second ionization chamber 4' detect the iron fluorescence radiation 106. The iron fluorescence radiation is reduced with an increasing zinc layer and is attenuated beginning at a layer thickness of approximately 300 $g/m^2$ to approximately 350 $g/m^2$ almost completely. The first ionization chamber 4 and the second ionization chamber 4' may determine zinc layers up to 350 $g/m^2$. The third ionization chamber 6 and the fourth ionization chamber 6' determine higher energy radiation, for example the due to Compton scattering. It is to be understood that the third ionization chamber 6 and the fourth ionization chamber 6' detect further components of scattering, such as scattering at atoms. The Compton scattering is also reduced by an increasing thickness of the zinc layer. Since the Compton scattering is on a higher energy level, it comprises a higher depth of penetration and accordingly a lower attenuation due to the zinc material. By the Compton effect a zinc layer having a thickness of up to 800 $g/m^2$ and approximately 1000 $g/m^2$, respectively may be detected.

The first and second ionization chamber 4, 4' are particularly suited for measuring thin zinc layers 18a, whereas the third and fourth ionization chamber 6, 6' are particularly suited for measuring thicker zinc layers.

Figure 3:
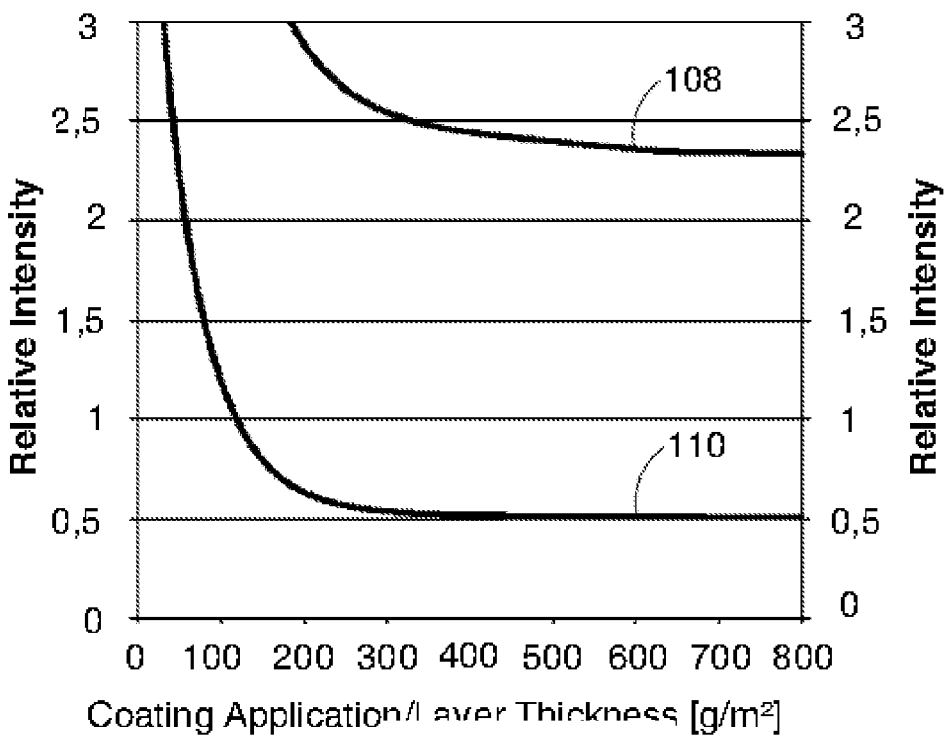
FIG. 3 shows measurement plots of the ionization chamber of the zinc thickness determination apparatus.

In FIG. 3 a line 110 shows the signal intensity of the first and second ionization chamber 4, 4' depending on the thickness of the zinc layer. Line 108 shows the signal intensity of the third and force ionization chamber 6, 6'. It is to be noted that due to the different filters 8, 10 the ionization chambers measure different types of radiation, since there sensitivity is located in the different energy ranges. The sensitivity of the first and second ionization chamber 4, 4' is allocated in a comparably low energetic level to detect the fluorescence radiation of iron. The sensitivity of the third and fourth ionization chamber 6, 6' is located in a comparably high energetic level in order to detect the Compton scattering of iron. Due to the slope of the signal 110 in the first and second ionization chamber 4, 4', the signal may be used for determining the thickness of a layer of zinc in a range from approximately 0 to approximately 350 g/m².

The signal of the third and forth ionization chamber 6, 6' may used in a range from approximately 200 g/m² to approximately 800 g/m² for determining the thickness of the zinc layer.

The first analyzing device 24a may be adapted to use in case of a thickness of the zinc layer which is lower than a predetermined threshold value, such as approximately 250 g/m², merely use the measurement signal due to iron fluorescence radiation that is detected by the first and second ionization chamber 4, 4'. The first analyzing device 24a may be adapted to determine in a range above a predetermined threshold value of the thickness of the zinc layer, such as more than 250 g/m², merely the Compton scattering, which is detected by the third and fourth ionization chambers 6, 6'.

The first analyzing device 24 a may be adapted to command the high-voltage device 20 a lower high-voltage to be supplied to the x-ray source 2, if the thickness of the test object is below a predetermined threshold value. The first analyzing device 24a can command the high-voltage device 20, to supply a higher voltage to the x-ray source 2, if the thickness of the sheet exceeds a threshold value. The lower x-ray voltage and high-voltage, respectively may be approximately 30 kV and the higher x-ray voltage and high-voltage, respectively may be 40 kV. Thereby, it can be avoided that the materials are completely radiographed. Generally, thinner materials comprise a thinner the zinc layer.

The first analyzing device 24a can use both the iron fluorescence radiation and the Compton scattering for determining the thickness of the zinc layer. In such case the first analyzing device 24a commands the high-voltage device 20 to drive the x-ray source 2 with a higher high voltage, such as 40 kV. If the thickness of the zinc layer is below a first threshold value, the thickness of the zinc layer is determined merely by the iron fluorescence radiation. If the thickness of the zinc layer is above a second threshold value, the thickness of the zinc layer is determined merely based on the Compton scattering. If the thickness of the zinc layer is below the first and second threshold value, both the iron fluorescence radiation and the Compton scattering is used to determine the thickness of the zinc layer.

The first analyzing device 24a can determine the thickness of the zinc layer merely based on iron fluorescence radiation, if the iron fluorescence radiation and/or the Compton scattering are above a first threshold value. The first analyzing device 24a can determine the thickness of the zinc layer merely by Compton scattering, if the iron fluorescence radiation and/or the Compton scattering are below a second threshold value. The first analyzing device 24a can use both the iron fluorescence radiation and the Compton scattering to determine the thickness of the zinc layer, if the iron fluorescence radiation and/or the Compton scattering are between the first and second threshold value.

The first analyzing device 24a can determine the thickness of the zinc layer by means of a weighted averaging from the iron fluorescence radiation and the Compton scattering. Hereby, the following from may be used:

$$x = \mu \cdot xc + (1-\mu) \cdot xf; \quad (1)$$

wherein:
xc: thickness measurement result based on Compton scattering;
xf: thickness measurement result based on iron fluorescence radiation;

Case 1: Selection due to the thickness measurement result based on Compton scattering:
$\mu=1$ for xc>first threshold value SW1;
$\mu=0$ für xc<second threshold value SW2; and
$\mu=(xc-SW1)/(SW2-SW1)$ for SW1≥xc≥SW2 case 2: 1: Selection due to the thickness measurement result based on iron fluorescence radiation:
$\mu=1$ for xf>first threshold value SW1;
$\mu=0$ for xf<second threshold value SW2; and
$\mu=(xf-SW1)/(SW2-SW1)$ for SW1≥xf≥SW2.

The first threshold value may be approximately 220 g/m² and the second threshold value can be approximately 350 g/m².

The first analyzing device 24a may determine the thickness of the zinc layer by means of a recursive approach. The expected measurement plots of the measurement signal depending on the thickness of the zinc layer may be stored in form of a table or of formulas $U_f=f_f(x)$ and $U_c=f_c(x)$. $U_f$ is the signal of the iron fluorescence radiation depending on the thickness of the zinc layer x, and $U_c$ is the signal due to Compton scattering depending on the thickness x. From the signals of the first and second ionization chamber 4, 4' results a signal $U_{sf}$ and from the third and fourth ionization chamber 6, 6' results the signal of the $U_{sc}$. It has to be determined, at which thickness the condition $f_f(x)-U_{sf}=0$ and $f_c(x)-U_{sc}=0$ are fulfilled. The zero points can be determined by the secant method (regula falsi), for example that is based on the Newton method.

The advantage of this method is that corrections of the function $f_f(x)$ and $f_c(x)$, which depend on x may be introduced easily. This relates particularly to distance corrections h(x, d) or scaling. The signals U from the ionization chambers depend also from the distance d of the test object from the determining device. This dependency is minimized by design. However, a residual dependency h(x, d) remains which is both a function of the distance as well as of the thickness x. This dependency can be determined for the determination device by a test equipment and thus, the function h(x, d) is known. This scaling is a function of the thickness x and is determined by using reference samples by calibration. During setup of the detection device after its making a calibration curve is determined. Thereafter, the scaling is 1. During operation of the detection device there is inevitably a shift of the detection device due to aging of the components or due to contamination. This shift is accommodated by calibrating the detection device by a scaling function n(x).

For example, by a measuring of samples having a known thickness the scaling function n(x) over the zinc layer thickness results and this scaling function is determined with the reference samples by calibration. During setup of the determining device after its making a calibration curve is created. Thereafter, the scaling is 1. During operation of the detection device a shift of the detection device due to aging of the components or due to contamination occurs.

Thereafter, the scaling function is an independent function of the thickness of the layer. In the case of influences of alloys, which are parameterized by the alloy portion p of the second components, such as the second layer (iron), the original function for detectors signals $U_{1,2}=f_{1,2}(x)$ may be supplemented by the additional function $g_{1,2}(x, p)$. Thus, in case of a galvannealing layer the determination of the iron content a steep arranged detector and a flat arranged detector are commonly used. Good results may be achieved, if as additional function the functions $p \cdot g_1(x)$ and $p \cdot g_2(x)$, respectively may be used. Preferably the parameter p from the two equations for $U_1$ and $U_2$ shall be eliminated in an unambiguous manner. In case of the above mentioned additional function $p \cdot g_1(x)$ and $p \cdot g_2(x)$, respectively by eliminating of P results the following equation:

$$g_2(x) \cdot (U_1 - f_1(x)) - g_1(x) \cdot (U_2 - f_2(x)) = 0;$$

The equation is again a zero points problem and may be solved by the above-mentioned second method (regula falsi). This may be solved in a program in the same single sequence. The zero point $x_n$ is already a solution for the layer thickness. The iron content p results then from the equation:

$$p = (U_1 - f_1(xn))/g_1(xn);$$

In case of influences from alloys, which may be parameterized by the alloy portion p of the second component, such as the second layer (iron), the original function $f_f(x)$ and $f_c(x)$ may be complimented additionally by the additional function $g_f(x, p)$ and $g_c(x, p)$. In case of a galvanneal layer for which the zinc layer and its iron content are determined, as is described below, good results may be achieved, when as additional function the functions $p\ g_f(x)$ and $p\ g_c(x)$ may be used. The parameter p represents the content of iron in the zinc layer.

The zinc thickness determination device may be calibrated by measuring 4 to 6 sheet samples with a known layer thickness. Thereby, the zinc thickness determination device 1 is positioned by means of a mechanic device over the sheet samples (reference samples). An iron sheet is used as first reference sample. Further, sufficiently thick zinc sheets are used as reference samples. This yields into the starting point of the curve and to the asymptote thereof. Additionally, the shields from a manufacturing process are used for calibrating, as long as they are uniform enough. If such reference samples are not available, zinc sheets may be used on which an iron film (having a thickness of 25 µm+/−5 µm, for example) is affixed. Further, the reference samples may be a pure iron sheet, a pure zinc sheet or a set of sheets with zinc layers having different thickness.

Figure 4:
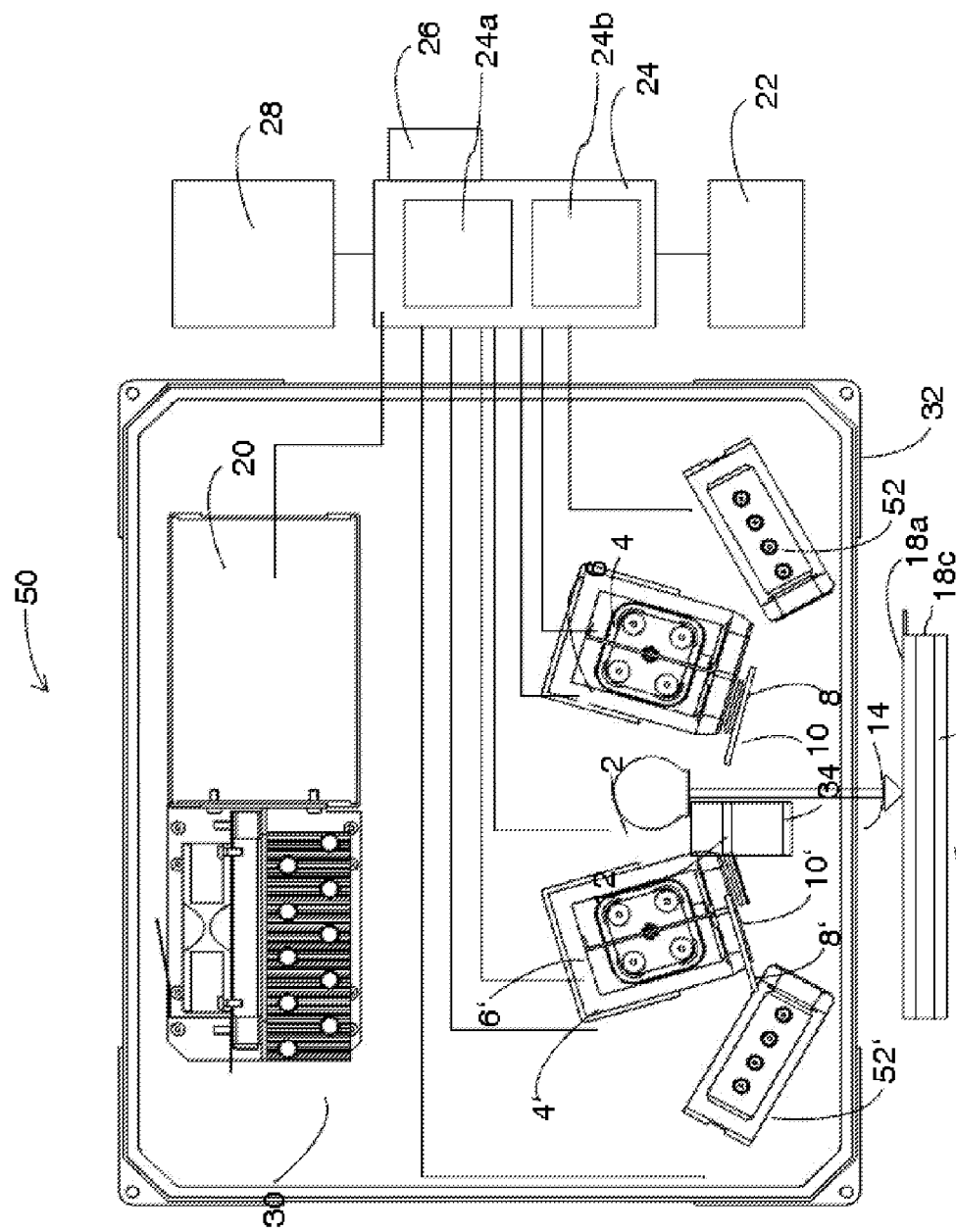
FIG. 4 shows a schematic view of the iron content determination apparatus.

FIG. 4 shows a determination apparatus 50 that is adapted to determine the thickness of a zinc layer 18*a* on an iron layer 18*b* and to detect the iron content 18*c* in the zinc layer 18*a* on the iron layer 18*b*. The determination device 50 comprises all components of the before described zinc thickness determination device 1, which are consequently not described anew for the sake of brevity of the specification.

Additionally, the determination device 50 comprises a first dispersive ionization chamber 52 and a second dispersive ionization chamber 52'. The dispersive ionization chambers 52, 52' comprise a plurality off ionization volumes, which may be read by a plurality of electrodes. Accordingly, beside the number of particles entering the ionization chamber also the energy distribution thereof may be determined. The dispersive ionization chamber 50, 52' each form an integrally formed second fluorescence detection device and the third fluorescence detection device. Both the first dispersive ionization chamber 52 and the second dispersive ionization chamber 52' can detect the fluorescence radiation of zinc and the fluorescence radiation of iron.

The first, second, third and fourth ionization chamber 4, 4', 6, 6' are arranged under a first angle and angle segment, respectively symmetrically to the x-ray beam 14, wherein the first angle is larger than 70° with respect to the surface of the test object 18, preferably approximately 80° with respect to the surface of the test object. The first dispersive ionization chamber 52 and the second dispersive ionization chamber 52' are arranged under a second angle and angle segment, respectively with respect to the surface of the test object 18. The first angle is lower than 35°, preferably 30°, most preferably lower than 30° with respect to the surface of the test object 18. The expression angle segment comprises marginal differences of the angles of the first, second, third and forth ionization chamber with respect to the surface of the test object.

The dispersive ionization chambers 52, 52' are arranged symmetrically to the x-ray beam 14 in order to cancel corrugations of the test object 18 and alignment errors.

For determining the iron content 18*c* in the zinc layer 18*a* the second determination device 24 uses the iron fluorescence signals from the first and second ionization chamber. Further, the second analyzing device 24*b* uses the value of the iron fluorescence radiation and the zinc fluorescence radiation measured by the dispersive ionization chambers 52, 52'.

The iron content of the zinc layer leads to an increased iron fluorescence radiation, to a reduced zinc fluorescence radiation and to an increased Compton scattering. Unfortunately this is also the case in a very similar manner due to reducing the thickness of the zinc layer. In order to resolve this ambiguity the measurement is supplemented by observing fluorescence radiation under a flat angle. A flat angle leads to an emphasize of the surface, since the observation depth in the perpendicular direction is reduced by the flat angle β corresponding to the equation $1/\cos(90-\beta)$. In other words, under the flat angle particularly the iron content in the zinc layer is determined in the detection device to a larger extent and additionally, respectively. A comparison between the determination in a steep angle and the determination in a flat angle resolves this ambiguity.

The second analyzing device can pass the iron content 18*c* in the zinc layer 18*a* to the first analyzing device for the determining the thickness of the zinc layer 18*a*, 18*c* more accurately.

Under reference to FIGS. 5 to 7 an exemplary ionization chamber 60 is disclosed. FIG. 5 shows side view of the dispersive ionization chamber, FIG. 6 shows a partly broken top view on the dispersive ionization chamber and FIG. 7 shows a front view of the dispersive ionization chamber 60. The x-ray radiation enters through a window 72 in an ionization zone 70 separated in a plurality of ionization volumes. An inert gas is ionized in the ionization zone by the entering x-ray radiation. A plurality of electrodes 60, 64, 66, 68 is assigned to the ionization volumes. On the housing 74 of the dispersive ionization chamber a voltage of approximately −150 V to approximately −300 V is applied.

X-ray radiation entering through the window 72 into the dispersive ionization chamber 60 passes first the ionization volume assigned to the first electrode 62. Further ionization volumes follow successively, which are each assigned to the second electrode 64, the third electrode 66 and the fourth electrode 68. X-ray radiation having lower energy is statistically absorbed in ionization volumes located more proximal to the window 72, whereas x-ray radiation having higher energy is statistically absorbed in ionization volumes assigned to electrodes located more distal from the window 72. Accordingly, it is possible to determine besides the intensity of the radiation also in the energy of the radiation, since the absorption of x-ray radiation having a lower energy causes with a higher likelihood an impulse at the electrodes 62, 64 located more proximal to the window, and x-ray radiation having higher energy is causing statistically with a higher likelihood an pulse at electrodes 66, 68 located more distal from the window 72. The operation point of the dispersive ionization chamber 60 may be parameterized by selecting a gas and an operational pressure. Each electrode may be connected to a current measuring device connected to ground. The absorption of the x-ray quanta generates charge detected by the electrodes 62, 64, 66, 68 and detected by the current measuring device assigned to the respective electrode.

Figure 8:
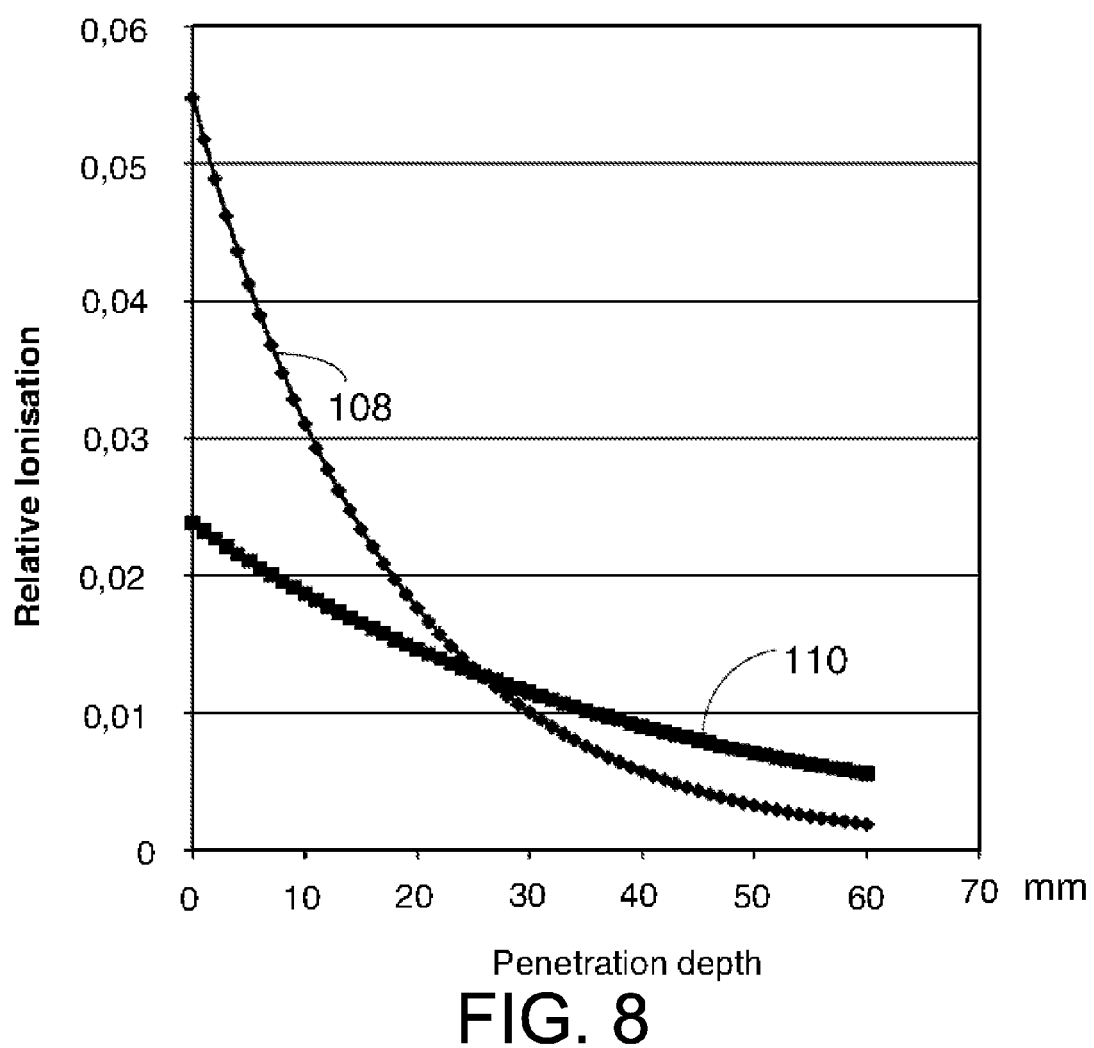
FIG. 8 shows the strength of the ionization as a function of the penetration depth in the dispersive ionization chamber.

FIG. 8 shows a plot in which the penetration depth of the x-ray radiation in the ionization zone 70 depending on the x-ray radiation is plotted. Argon having a pressure of approximately 1.6 bar is located in the ionization zone. The plot 108 results from the iron-K-alpha-line and from the iron-K-beta-line. The more flat plot results from the zinc-K-alpha-line and the zinc-K-beta-line. Since the zinc fluorescence radiation is statistically absorbed more distal from the window 72, it comprises higher energy than the iron fluorescence radiation. Consequently, the dispersive ionization chamber allows determining the type of radiation.

Figure 9:
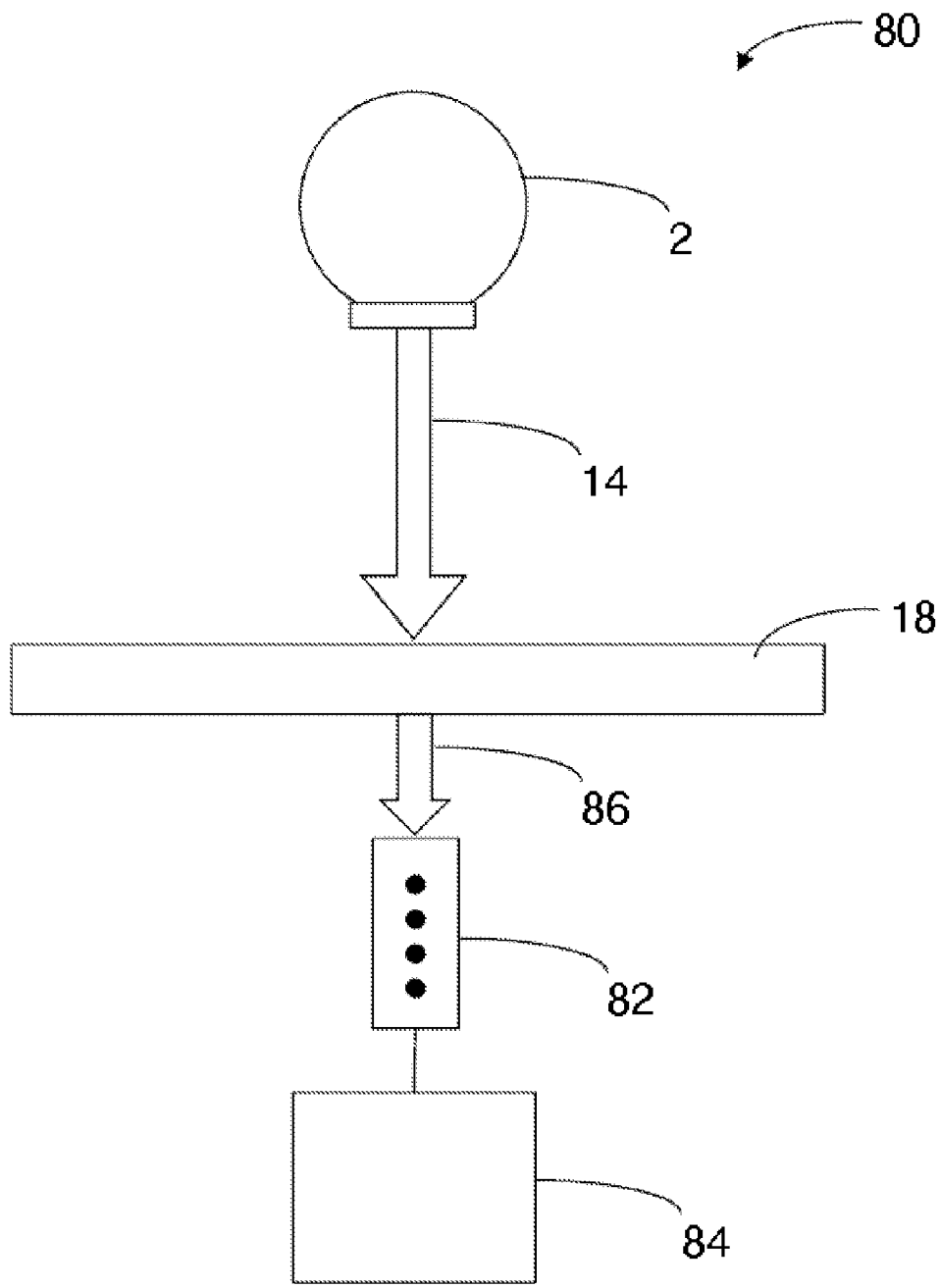
FIG. 9 shows a layer thickness measurement device having the dispersive ionization chamber.

FIG. 9 shows a further application of a dispersive ionization chamber for material testing. FIG. 9 shows a schematically a thickness determination apparatus 80. An x-ray source 2 emits a primary x-ray beam 14 to a test object 18. The x-ray beam passes through the test object 18 and enters as secondary x-ray radiation 86 into the dispersive ionization chamber 82. The test object 18 may be sheet steel, for example. The ionization chamber 82 is connected to an analyzing device 84. Based on the ratio of penetration depth of the x-ray radiation and ionization in the dispersive ionization chamber 82 it can be determined, which materials are comprised by the test object. Accordingly, the analyzing device 84 can determine the value of the attenuation coefficient of the test object 18 for x-ray radiation. Thereafter, based on the sum of the absorbed x-ray radiation in the ionization chamber 82 as well as based on the attenuation coefficient(s) the thickness of the test object 18 can be determined.

The fluorescence detection device and the Compton detection device may be implemented by a single pulse counter, such as a semiconductor counter, as long as they are sufficiently stable and sufficiently resistant against aging.

The thickness of the zinc coating has been noted in the description in the unit grams per square meter. By the following formula the thickness can be transformed in the thickness in micrometers:

$$\text{Thickness [µm]} = \text{coating [g/m}^2\text{]}/\rho_{Layer}; \quad (2)$$

wherein $\rho_{Layer} = 7.1$ g/cm$^3$ for zinc.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. An apparatus configured as a determining device, adapted to determine the thickness of a zinc layer on an iron layer of a test object and the iron content in the zinc layer on the iron layer of the test object, comprising:
    an x-ray source, emitting x-ray radiation to the test object having the zinc layer on the iron layer;
    a first fluorescence detection device determining a first fluorescence radiation due to iron in the test object scattered under a first angle segment from the test object;
    a Compton radiation detection device determining a Compton scattering based on iron in a test object scattered under a first angle segment from the test object, the Compton detection device including:
        an x-ray sensor; and
        a filter arrangement adapted such that the radiation emitted by a test object due to Compton scattering passes a nickel layer and an iron layer before being detected by the x-ray sensor;
    a second fluorescence detection device determining a second fluorescence radiation due to iron in the test object scattered in a second angle segment from the test object;
    a third fluorescence detection device determining a third fluorescence radiation due to iron in the test object scattered in the second angle segment from the test object;
    a first analyzing device adapted to determine the thickness of the zinc layer on the iron layer of the test object based on the first fluorescence radiation and the Compton radiation; and
    a second analyzing device adapted to determine the iron content in the zinc layer based on the first fluorescence radiation, the second fluorescence radiation and the third fluorescence radiation.

2. The apparatus according to claim 1, wherein the sensor is an ionization chamber.

3. The apparatus according to claim 1, wherein the filter arrangement is adapted to suppress zinc fluorescence radiation.

4. The apparatus according to claim 1, wherein the first angle segment is in a range from approximately 45° to approximately 90° and/or the second angle segment is in a range from approximately 0° to approximately 45°.

5. The apparatus according to claim 1, wherein at least one of the fluorescence detection devices and/or the Compton detection device comprises a dispersive ionization chamber.

6. The apparatus according to claim 1, wherein the first analyzing device is adapted to determine a weighted average from the first fluorescence radiation and the Compton radiation in order to determine the thickness of the zinc layer.

7. The apparatus according to claim 1, wherein the first analyzing device is adapted to determine the thickness of the zinc layer recursively from the first fluorescence radiation and the Compton scattering.

8. The apparatus according to claim 1, wherein the first analyzing device is adapted to take into account the iron content in a zinc layer for determining the thickness of the zinc layer.

9. A determining device, adapted to determine the thickness of a zinc layer on an iron layer of a test object, comprising:
    an x-ray source, emitting x-ray radiation to the test object having the zinc layer on the iron layer;
    a first fluorescence detection device determining a first fluorescence radiation due to iron in the test object scattered under a first angle segment from the test object;
    a Compton radiation detection device determining a Compton scattering based on iron in a test object scattered under a first angle segment from the test object, the Compton detection device including:
        an x-ray sensor; and
        a filter arrangement adapted such that the radiation emitted by a test object due to Compton scattering passes a nickel layer and an iron layer before being detected by the x-ray sensor; and a first analyzing device adapted to determine the thickness of the zinc layer on the iron layer of the test object based on the first fluorescence radiation and the Compton radiation.

10. The determining device according to claim 9, wherein the first angle segment is in a range from approximately 45° to approximately 90° and/or the second angle segment is in a range from approximately 0° to approximately 45°.

11. The determining device according to claim 9, wherein at least one of fluorescence detection device and/or the Compton detection device comprises a dispersive ionization chamber.

12. The determining device according to claim 9, wherein the first analyzing device is adapted to determine a weighted average from the first fluorescence radiation and the Compton radiation in order to determine the thickness of the zinc layer.

13. The determining device according to claim 9, wherein the first analyzing device is adapted to determine the thickness of the zinc layer recursively from the first fluorescence radiation and the Compton scattering.

14. The determining device according to claim 9, wherein the first analyzing device is adapted to take into account the iron content in a zinc layer for determining the thickness of the zinc layer.

15. A dispersive ionization chamber, comprising
an ionization chamber having a plurality of ionization volumes, wherein each ionization volume comprises an electrode,
a window, through which x-ray radiation can enter,
wherein the ionization volumes are arranged in beam propagation direction behind each other, such that x-ray radiation having lower energy is statistically absorbed in ionization volumes located more proximal to the window, and x-ray radiation having higher energy is statistically absorbed in the ionization volumes located more distal from the window, the dispersive ionization chamber adapted to determine the thickness of a zinc layer on an iron layer of a test object, comprising:
an x-ray source, emitting x-ray radiation to the test object having the zinc layer on the iron layer;
a first fluorescence detection device determining a first fluorescence radiation due to iron in the test object scattered under a first angle segment from the test object;
a Compton detection device determining a Compton scattering based on iron in a test object scattered under a first angle segment from the test object, the Compton detection device including:
an x-ray sensor; and
a filter arrangement adapted such that the radiation emitted by a test object due to Compton scattering passes a nickel layer and an iron layer before being detected by the x-ray sensor; and a first analyzing device adapted to determine the thickness of the zinc layer on the iron layer of the test object from the first fluorescence radiation and the Compton radiation,
wherein at least one fluorescence detection device and/or the Compton detection device are formed by the dispersive ionization chamber.

16. The dispersive ionization chamber according to claim 15, wherein the electrodes are arranged in beam propagation direction behind each other.

17. The dispersive ionization chamber according to claim 15, wherein x-ray radiation entering through the window into the dispersive ionization chamber passes the ionization volume comprising the first electrode and successively further ionization volumes respectively comprising a second, a third and a fourth electrode.

18. The dispersive ionization chamber according to claim 15, wherein the ionization volumes are located in an ionization zone filled with the inert gas.

19. The dispersive ionization chamber according to claim 15, wherein a current measuring device is connected to each of the electrodes and wherein the dispersive ionization chamber is adapted such that an absorption of an x-ray quantum generates charge collected by one of the electrodes.

20. The dispersive ionization chamber according to claim 15, in which a dispersive ionization chamber is used for material testing.

21. The dispersive ionization chamber according to claim 15, configured as a material testing device having the dispersive ionization chamber.

22. The dispersive ionization chamber according to claim 15, configured as a thickness measuring device, comprising the dispersive ionization chamber.

23. The dispersive ionization chamber according to claim 15, adapted to determine the iron content in the zinc layer on the iron layer of the test object, comprising:
an x-ray source, emitting x-ray radiation to the test object having the zinc layer on the iron layer;
a first fluorescence detection device determining a first fluorescence radiation due to iron in the test object scattered under a first angle segment from the test object;
a second fluorescence detection device determining a second fluorescence radiation due to iron in the test object scattered in a second angle segment from the test object;
a third fluorescence detection device determining a third fluorescence radiation due to iron in the test object scattered in the second angle segment from the test object; and
a second analyzing device adapted to determine the iron content in the zinc layer from the first fluorescence radiation, the second fluorescence radiation and the third fluorescence radiation,
wherein at least one fluorescence detection device is formed by the dispersive ionization chamber.

* * * * *